(12) United States Patent
Mallela et al.

(10) Patent No.: US 8,846,915 B2
(45) Date of Patent: Sep. 30, 2014

(54) PROCESS FOR THE MANUFACTURE OF ROSUVASTATIN CALCIUM USING CRYSTALLINE ROSUVASTATIN ETHYL ESTER

(75) Inventors: Sambhu Prasad Sarma Mallela, Hyderabad (IN); Sukumar Nandi, Hyderabad (IN); Ganagadnar Bhima Shankar Nangi, Hyderabad (IN); Ramesh Dandala, Hyderabad (IN); Sivakumaran Meenakshisunderam, Hyderabad (IN)

(73) Assignee: Aurobindo Pharma Ltd., Hyderabad (IN)

( * ) Notice: Subject to any disclaimer, the term of this patent is extended or adjusted under 35 U.S.C. 154(b) by 169 days.

(21) Appl. No.: 13/261,184

(22) PCT Filed: Aug. 17, 2009

(86) PCT No.: PCT/IB2009/006580
§ 371 (c)(1), (2), (4) Date: Feb. 16, 2012

(87) PCT Pub. No.: WO2011/021058
PCT Pub. Date: Feb. 24, 2011

(65) Prior Publication Data
US 2012/0149905 A1    Jun. 14, 2012

(51) Int. Cl.
C07D 239/24   (2006.01)
C07D 239/42   (2006.01)

(52) U.S. Cl.
CPC ................................ *C07D 239/42* (2013.01)
USPC ........................................................ 544/332

(58) Field of Classification Search
USPC ........................................................ 544/332
See application file for complete search history.

(56) References Cited

U.S. PATENT DOCUMENTS

| | | |
|---|---|---|
| RE37,314 E | 8/2001 | Hirai |
| 2008/0188504 A1 | 8/2008 | Casar |
| 2008/0255170 A1 | 10/2008 | Zlicar |
| 2010/0197916 A1 | 8/2010 | Niddam-Hildesheim |
| 2010/0228028 A1 | 9/2010 | Butters |

FOREIGN PATENT DOCUMENTS

| | | |
|---|---|---|
| WO | WO2005/042522 A1 | 5/2005 |
| WO | WO2006/100689 A1 | 9/2006 |
| WO | WO2007/040940 A1 | 4/2007 |
| WO | 2009118598 | * 10/2009 |

* cited by examiner

*Primary Examiner* — James O Wilson
*Assistant Examiner* — Ebenezer O Sackey
(74) *Attorney, Agent, or Firm* — Jay R Akhave

(57) ABSTRACT

The present invention relates to an improved process to prepare Rosuvastatin calcium of Formula (I), with good quality. Further, the present invention also relates to a crystalline polymorphic form of Rosuvastatin ethyl ester.

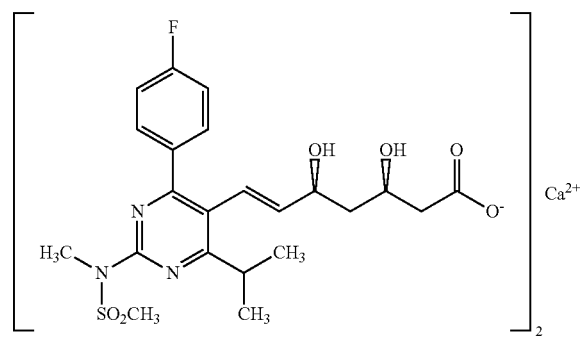

(I)

20 Claims, 4 Drawing Sheets

PROCESS FOR THE MANUFACTURE OF ROSUVASTATIN CALCIUM USING CRYSTALLINE ROSUVASTATIN ETHYL ESTER

This application is national phase application of the International Application No. PCT/IB2009/006580, filed on Aug. 17, 2009.

FIELD OF THE INVENTION

The present invention relates to an improved process to prepare Rosuvastatin calcium of Formula I.

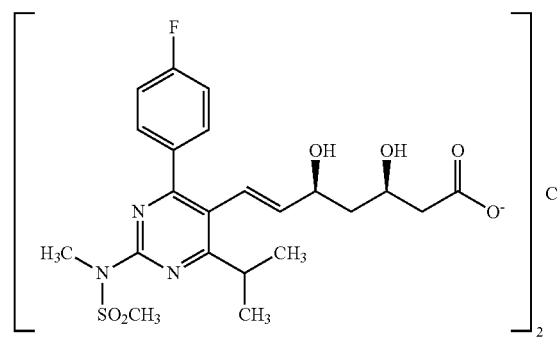

Formula I

BACKGROUND OF THE INVENTION

Rosuvastatin, which is an antihyperchlolesterolemic drug, is chemically known as (E)-7-[4-(4-fluorophenyl)-6-isopropyl-2-[methyl(methylsulfonyl)amino]-pyrimidin-5-yl]-(3R,5S)-3,5-dihydroxy-hept-6-enoic acid calcium (2:1) salt of Formula I.

Rosuvastatin is enantiomerically pure compound having two chiral centers in the side chain of the molecule. All four isomers of Rosuvastatin can be separated by HPLC.

The synthetic process for preparing Rosuvastatin Calcium is disclosed in U.S. Pat. No. RE 37,314 E, which involves reduction of 5-keto-3(R)-hydroxy Rosuvastatin methyl ester using sodium borohydride and diethylmethoxyborane in presence of tetrahydrofuran and methanol.

WO 2005/042522 A1 discloses crystalline compound of ethyl-(E)-7-[4-(4-fluorophenyl)-6-isopropyl-2-[methyl(methylsulfonyl)amino]pyrimidin-5-yl] (3R,5S)-3,5-dihydroxy-hept-6-enoate having an X-ray powder diffraction pattern with peaks at 2-theta 4.3, 8.1, 11.3, 12.4, 15.1, 19.9, 21.0, 21.7, 22.1 and 23.5. The process is as summarized below:

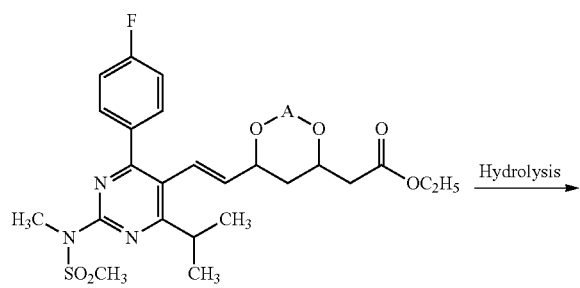

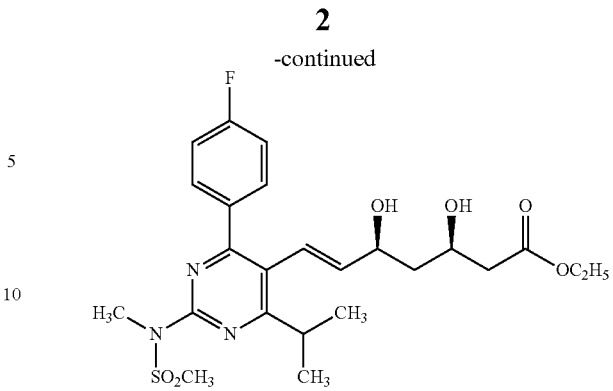

i) Hydrochloric acid Acetonitrile
ii) Sodium chloride in water
iii) Evaporation
iv) Purified on silica
v) 1.1 mixture of iso-hexane:toluene

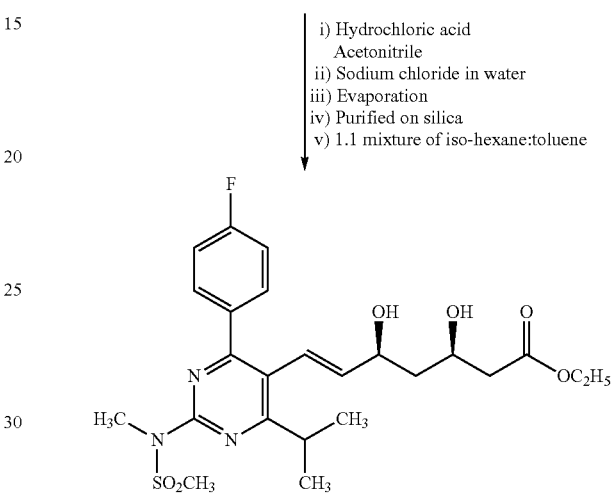

WO 2006/100689 A1 discloses a process to prepare Rosuvastatin alkyl ester from Rosuvastatin keto ester by combining Rosuvastatin keto ester, diethylmethoxy borane in tetrahydrofuran and methanol. Thereafter, sodium borohydride was added to the above reaction mass and stirred to obtain Rosuvastatin alkyl ester. HPLC analysis of the Rosuvastatin alkyl ester produced by the method disclosed above revealed that the reduction did not go to completion and the resulting Rosuvastatin alkyl ester is contaminated with unreacted starting material and also high level of diastereomeric impurity. It is tedious to separate these impurities by the conventional purification techniques. Therefore, we realized that there is a need for reduction, which gives pure Rosuvastatin alkyl ester.

WO 2007/040940 A1 discloses a process to prepare Rosuvastatin alkyl ester from Rosuvastatin keto ester by combining MeO-9-BBN or diethylmethoxyborane with an organic solvent selected from a group consisting of methylene chloride, toluene, methyl t-butyl ether, diethyl ether, tetrahydrofuran, dioxane, methanol, ethanol, isopropanol, n-butanol; and a source of hydride ion and then adding to the said combination to a solution of a Rosuvastatin keto ester in an organic solvent to obtain a reaction mixture. Thereafter, the reaction mixture was maintained to obtain Rosuvastatin alkyl ester. Analysis of the product obtained by the above process revealed that the presence of unreacted starting material in the product, which was difficult to separate by normal crystallization techniques.

Therefore, we report herein a new crystalline form of Rosuvastatin ethyl ester and also a process to prepare Rosuvastatin alkyl esters having low level of diastereomeric impurity and other impurities, which can give Rosuvastatin calcium with desired quality.

OBJECTIVE

The objective of the present invention is to provide an improved process for preparing Rosuvastatin calcium with high yield and high purity.

In yet another objective of the present invention is to provide an improved process for preparing Rosuvastatin, which is simple, industrially applicable and economically viable.

In yet another objective of the present invention is to provide new crystalline form of Rosuvastatin ethyl ester.

SUMMARY OF THE INVENTION

Figure 1:
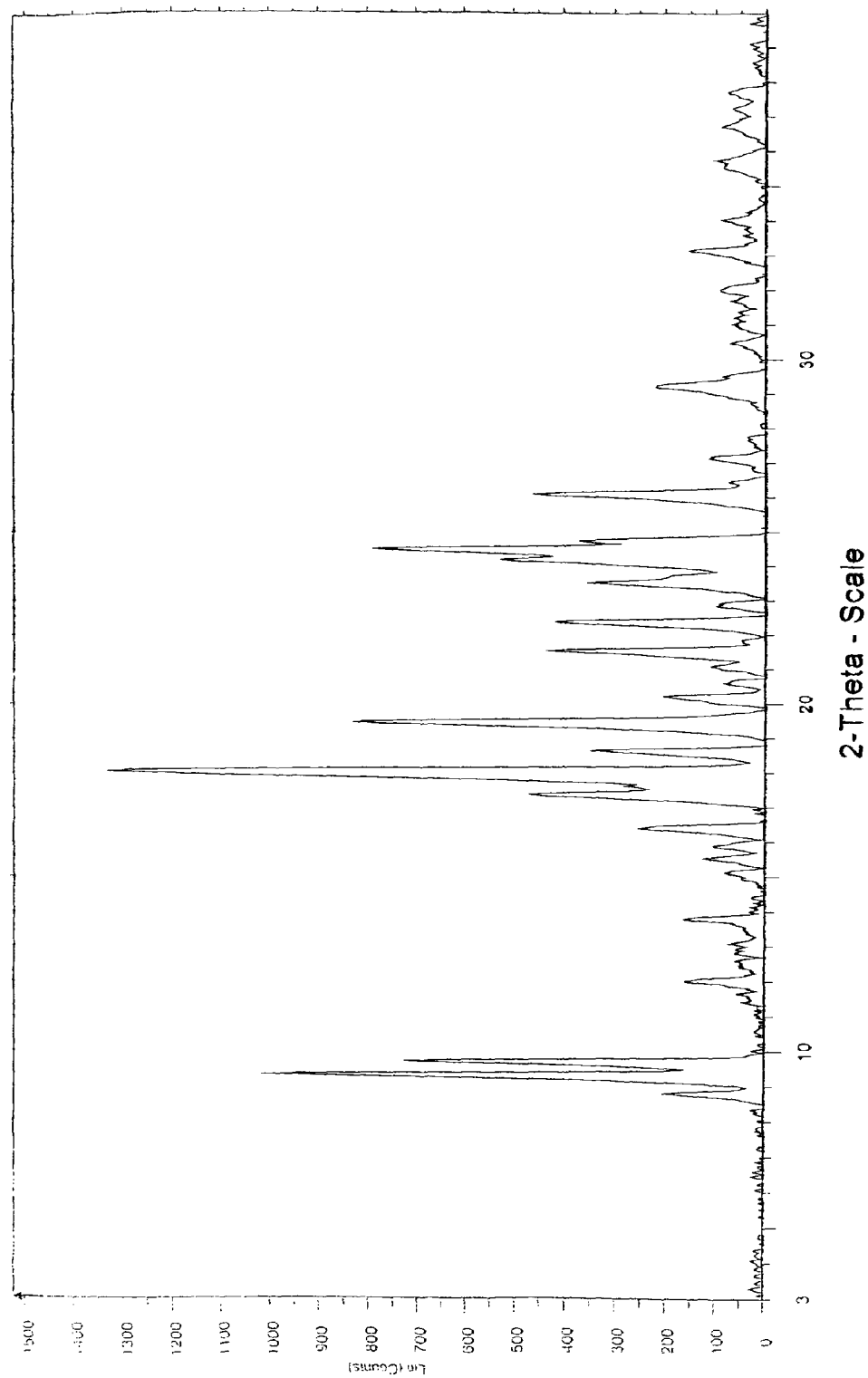
FIG. 1—Powder X-ray diffraction (PXRD) of Rosuvastatin ethyl ester according to example 6
Figure 2:
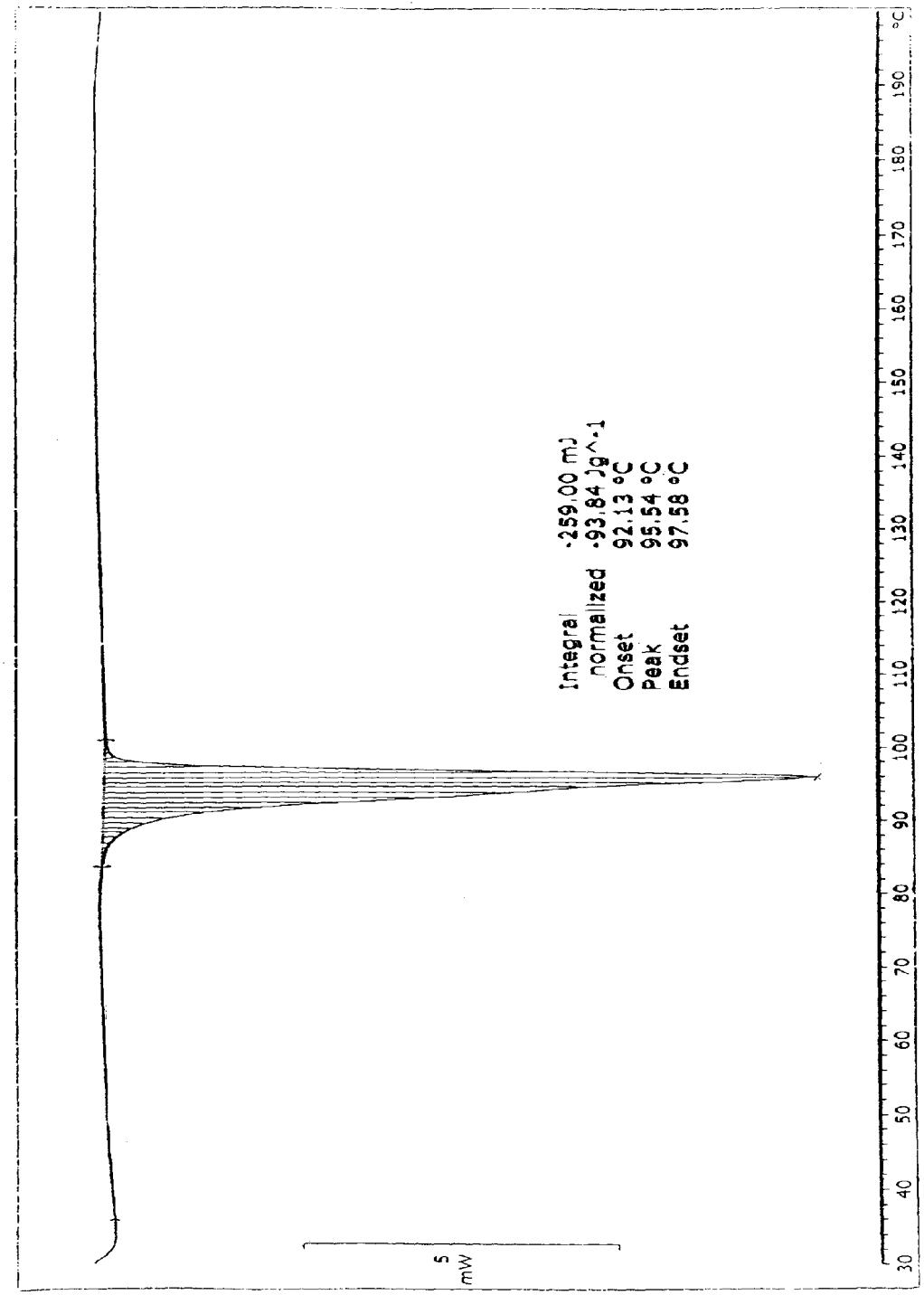
FIG. 2—Differential Scanning calorimetry (DSC) of Rosuvastatin ethyl ester according to example 6
Figure 3:
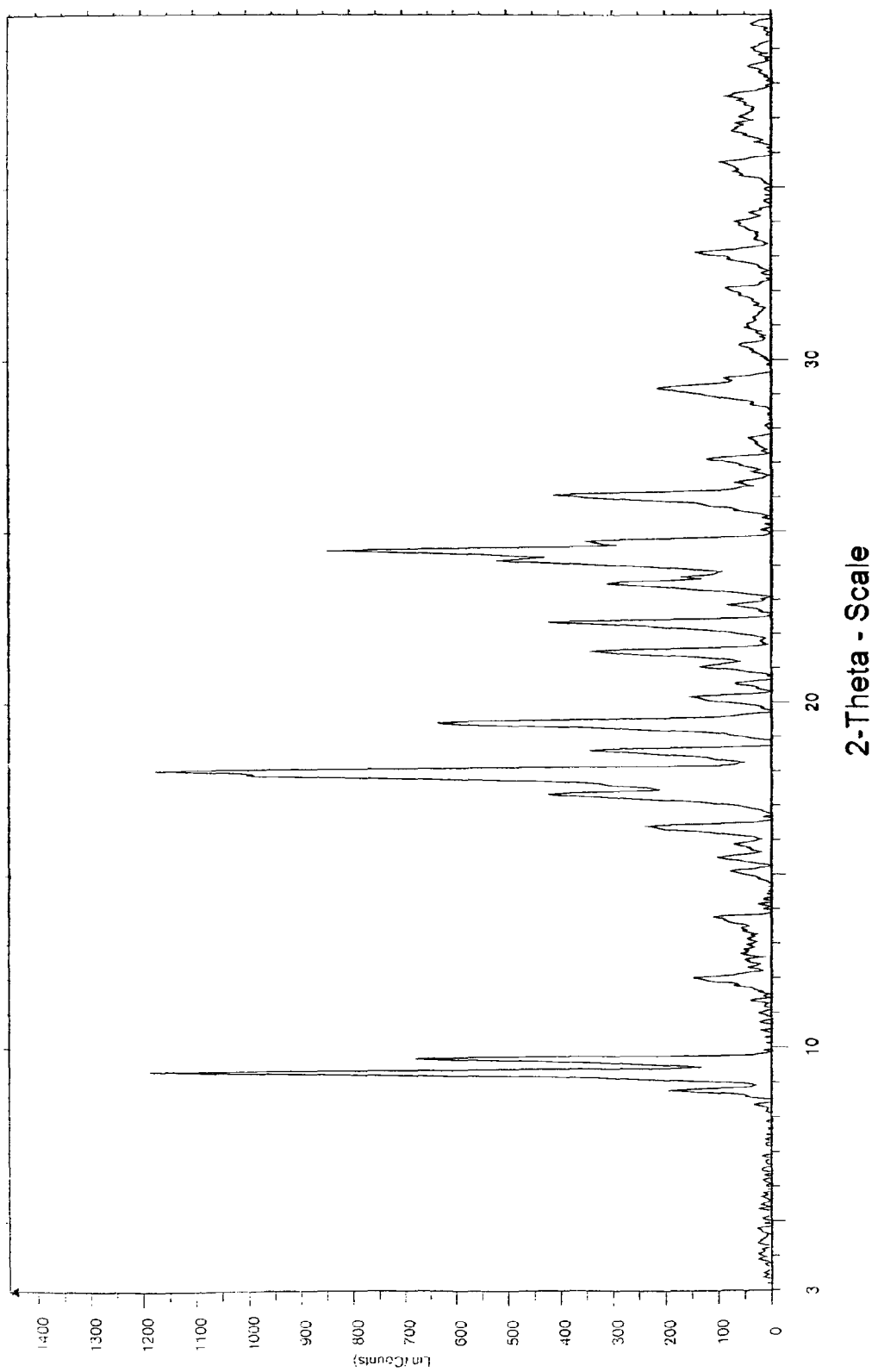
FIG. 3—Powder X-ray diffraction (PXRD) of Rosuvastatin ethyl ester according to example 7
Figure 4:
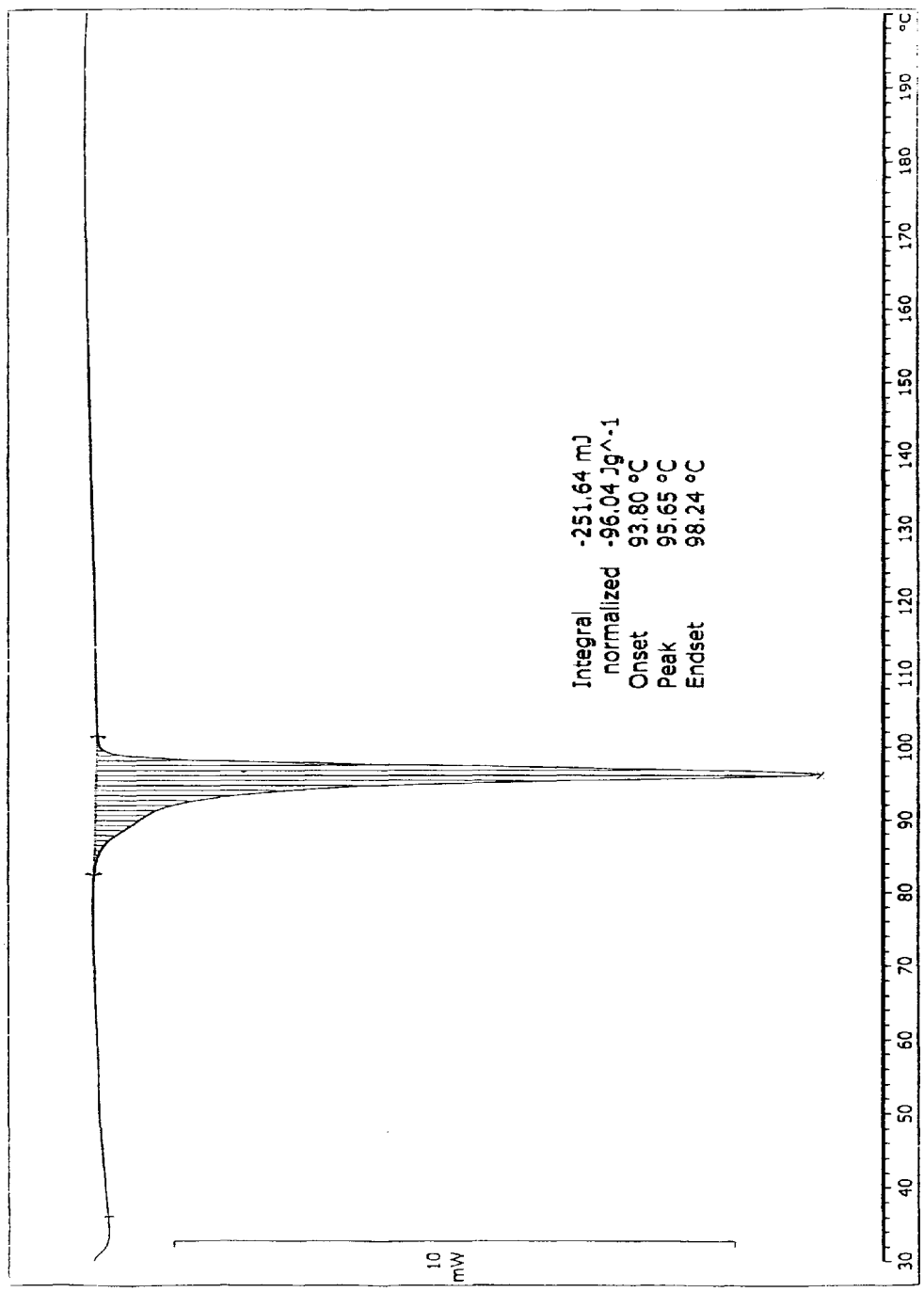
FIG. 4—Differential Scanning calorimetry (DSC) of Rosuvastatin ethyl ester according to example 7

The present invention relates to an improved process for preparing Rosuvastatin alkyl ester of Formula II,

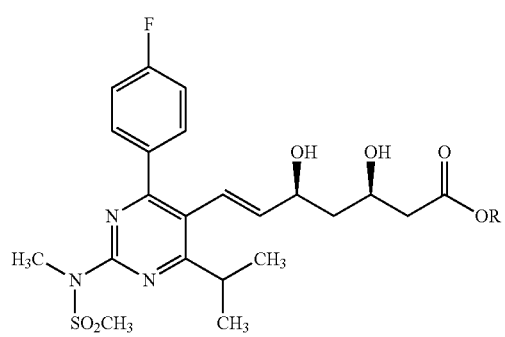

Formula II wherein R represents straight or branched $C_{1-5}$ alkyl, aryl, aralkyl which comprises:

a) reducing Rosuvastatin keto ester of Formula III

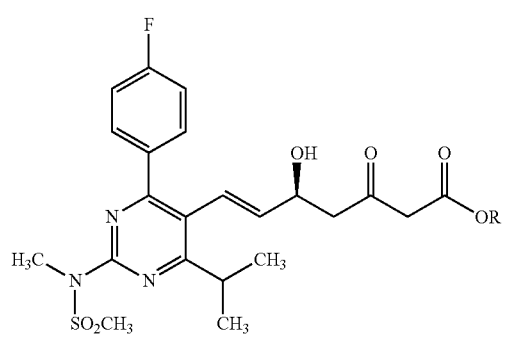

Formula III with a hydride ion source and dialkylalkoxyborane at low temperature in a mixture of three or more organic solvents selected each from an ethereal solvent, alcoholic solvent and an aprotic solvent;

b) maintaining the reaction mass at the same temperature under stirring for completion of reaction;

c) isolating the compound of Formula II.

The present invention also relates to an improved process for preparing

Rosuvastatin alkyl ester of Formula II,

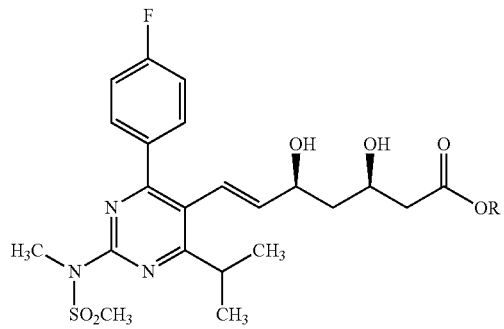

Formula II wherein R represents straight or branched $C_{1-5}$ alkyl, aryl, aralkyl which comprises:

a) combining Rosuvastatin keto ester of Formula III

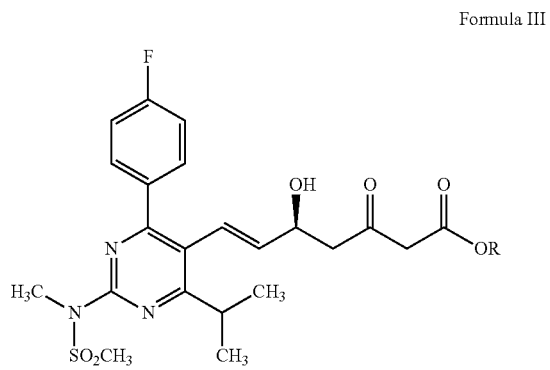

Formula III with dialkylalkoxyborane at low temperature in a mixture of three or more organic solvents selected each from an ethereal solvent, alcoholic solvent and an aprotic solvent;

b) adding hydride ion source at temperature ranging from −50° C. to −90° C. to step (a) mixture;

c) maintaining the reaction mass at the same temperature under stirring for completion of reaction;

d) quenching the reaction mass with water or acids such as acetic acid, trifluoroacetic acid or bases like aqueous sodium bicarbonate, potassium carbonate or peroxide like aqueous hydrogen peroxide and the like to obtain compound of Formula II.

The present invention also relates to an improved process for preparing Rosuvastatin alkyl ester of Formula II, Formula II

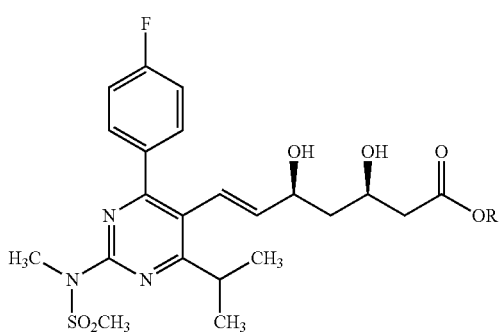

wherein R represents straight or branched $C_{1-5}$ alkyl, aryl, aralkyl which comprises:
a) combining dialkylalkoxyborane, hydride ion source at low temperature in a mixture of three or more organic solvents selected each from an ethereal solvent, alcoholic solvent and an aprotic solvent;
b) adding a solution of Rosuvastatin keto ester of Formula III Formula III

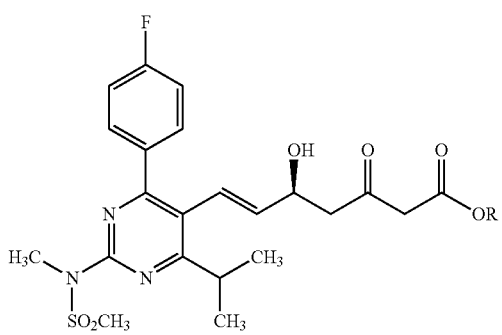

to step (a) mixture;
c) maintaining the reaction mass at the same temperature under stirring for completion of reaction;
d) quenching the reaction mass with water or acids such as acetic acid, trifluoroacetic acid or bases like aqueous sodium bicarbonate, potassium carbonate or peroxide like aqueous hydrogen peroxide and the like to obtain compound of Formula II.

In another embodiment, the present invention also provides further conversion of Rosuvastatin alkyl ester of Formula II to Rosuvastatin calcium, with high purity.

In another embodiment, the present invention also provides new crystalline polymorphic form of Rosuvastatin ethyl ester of Formula II.

In yet another embodiment, the present invention relates to new crystalline polymorphic form of Rosuvastatin ethyl ester of Formula II, having a X-ray Powder Diffraction having peak reflections at about 9.2, 9.6, 17.3, 18.0, 18.6, 19.4, 21.5, 22.3, 24.2, 24.4, 26.0±0.2 degrees two-theta.

In yet another embodiment, the crystalline polymorphic form of Rosuvastatin ethyl ester of Formula II, is further characterized by having X-ray Powder Diffraction peak reflections at about 8.7, 12.0, 13.7, 15.1, 15.5, 15.8, 16.4, 20.2, 20.6, 21.0, 22.9, 23.5, 24.7, 27.1, 29.2, 30.5, 32.0, 33.1±0.2 degrees two-theta.

DETAILED DESCRIPTION OF THE INVENTION

The present invention relates to new crystalline polymorphic form of Rosuvastatin ethyl ester of Formula II, having a X-ray Powder Diffraction having peak reflections at about 9.2, 9.6, 17.3, 18.0, 18.6, 19.4, 21.5, 22.3, 24.2, 24.4, 26.0±0.2 degrees two-theta.

In another embodiment, the crystalline polymorphic form of Rosuvastatin ethyl ester of Formula II, is further characterized by having X-ray Powder Diffraction peak reflections at about 8.7, 12.0, 13.7, 15.1, 15.5, 15.8, 16.4, 20.2, 20.6, 21.0, 22.9, 23.5, 24.7, 27.1, 29.2, 30.5, 32.0, 33.1±0.2 degrees two-theta.

In another embodiment, crystalline polymorphic form of Rosuvastatin ethyl ester of Formula II, is further characterized by having a Differencial Scanning calorimetry (DSC) endothermic peak at about 95.5° C.±1° C.

The present invention relates to an improved process for the preparation of Rosuvastatin alkyl ester of Formula II, which comprises preparing a solution of Rosuvastatin keto ester of Formula III in an organic solvent or a mixture of organic solvents and adding a solution of dialkylalkoxyborane in a mixture of three or more organic solvents at low temperature to the above solution.

Thereafter, the reaction mass is stirred at same temperature and treated with a source of hydride ion. The organic solvent is selected from the group consisting of an ethereal solvent selected from $C_2$-$C_8$ ethers or cyclic ethers such as diethyl ether, dimethyl ether, tetrahydrofuran; alcoholic solvent selected from $C_1$-$C_4$ alcohol such as methanol, ethanol, butanol and aprotic solvents such as toluene, alkyl esters such as ethyl acetate, methyl acetate, chlorinated solvents such as methylene chloride, chloroform.

The present invention relates to an improved process for the preparation of Rosuvastatin alkyl ester of Formula II, which comprises providing a solution of dialkylalkoxyborane and source of hydride ion at low temperature in a mixture of three or more organic solvents. Dissolving Rosuvastatin keto ester of Formula III in an organic solvent or a mixture of organic solvents and adding this solution to above solution at low temperature. Thereafter, the reaction mass is stirred to yield Rosuvastatin alkyl ester of Formula II. The organic solvent is selected from the group consisting of an ethereal solvent selected from $C_2$-$C_8$ ethers or cyclic ethers such as diethyl ether, dimethyl ether, tetrahydrofuran; alcoholic solvent selected from $C_1$-$C_4$ alcohol such as methanol, ethanol, butanol and aprotic solvents such as toluene, alkyl esters such as ethyl acetate, methyl acetate, chlorinated solvents such as methylene chloride, chloroform.

The dialkylalkoxyborane is selected from diethylmethoxyborane, dimethylmethoxyborane, diethylethoxyborane, dimethylethoxyborane. Preferably diethylmethoxyborane is used as chelating agent.

A solution of dialkylalkoxyborane is prepared by adding a tetrahydrofuran solution of dialkylalkoxyborane to a solvent mixture selected from the group consisting of an ethereal solvent selected from $C_2$-$C_8$ ethers or cyclic ethers such as diethyl ether, dimethyl ether, tetrahydrofuran; alcoholic solvent selected from $C_1$-$C_4$ alcohol such as methanol, ethanol, butanol and aprotic solvents such as toluene, alkyl esters such as ethyl acetate, methyl acetate, chlorinated solvents such as methylene chloride, chloroform; or mixture of three or more solvents.

The three preferred solvents are tetrahydrofuran, methanol and ethyl acetate or tetrahydrofuran, methanol and toluene. The chelating agent used is in the range of 1-10 m. eq. based on Rosuvastatin keto ester of Formula III.

Preferably, the total volume of solvent used for the preparation of Rosuvastatin keto ester of Formula III and dialkylalkoxyborane is about 10 volumes to 80 volumes (ml per gram of Rosuvastatin keto ester of Formula III) in the reaction mixture, more preferably 30-40 volumes.

Source of hydride ion is selected from a group consisting of sodium borohydride, potassium borohydride, lithium borohydride and sodium triacetoxyborohydride preferably the source of hydride ion is present in an amount of 1 to about 4 equivalent (per gram of Rosuvastatin keto ester of Formula III). The solvents used in the present invention should not decompose hydride ion source.

The temperature during the mixing of Rosuvastatin keto ester of Formula III solution with diethylmethoxyborane solution and also while adding hydride ion source is preferably in the range of −50° C. to −95° C., more preferably −70° C. to −80° C.

The reaction mixture is maintained for 30 min to 8 h; preferably 5-6 h at temperature −70° C. to −80° C.

Reaction is quenched at −80° C. to −50° C. by adding quenching agent to the reaction mass. The quenching agent is selected from water, acetic acid, aqueous hydrochloric acid, acetone, trifluoroacetic acid, aqueous hydrogen peroxide, ammonium chloride, sodium bicarbonate, aqueous acidic buffer or mixture thereof. Preferred agents are acidic buffer or acetic acid.

Aqueous acidic buffer is made from potassium dihydrogen phosphate, triethyl amine and orthophosphoric acid having pH in the range of 2-4.

After quenching the reaction, the reaction mass is diluted with water and extracted with solvents like ethyl acetate, toluene, methylene chloride and the like and preferably with ethyl acetate.

Another embodiment of the invention provides a process for improving the quality of the Rosuvastatin alkyl ester of Formula II, by recrystallization.

The recrystallization process of Rosuvastatin alkyl ester of Formula II, comprises:
a) preparing a solution of Rosuvastatin alkyl ester of Formula II, in an organic solvent selected from $C_1$-$C_5$ alcohol such as methanol, ethanol, butanol; $C_3$-$C_8$ esters such as ethyl acetate, methyl acetate; $C_3$-$C_8$ ketones such as methylethyl ketone, methylisobutyl ketone, acetone; $C_6$-$C_{10}$ aromatic hydrocarbons such as toluene; ethers such as tetrahydrofuran, methylethyl ether; acetonitrile and mixture thereof and cooling the mass to give Rosuvastatin alkyl ester of Formula II.

Another recrystallization process of Rosuvastatin alkyl ester of Formula II, which comprises:
a) preparing a solution of Rosuvastatin alkyl ester of Formula II, in an organic solvent selected from $C_1$-$C_5$ alcohol such as methanol, ethanol, butanol; $C_3$-$C_8$ esters such as ethyl acetate, methyl acetate; $C_3$-$C_8$ ketones such as methylethyl ketone, methylisobutyl ketone, acetone; $C_6$-$C_{10}$ aromatic hydrocarbons such as toluene, anisole; ethers such as tetrahydrofuran, methylethyl ether; acetonitrile and mixture thereof;
b) treating the above solution from step (a) with an anti solvent like aliphatic hydrocarbons like, pentane, hexane, heptane, cyclohexane and the like;
c) stirring the resulting slurry from step (b) for 1 h to 48 h to give pure Rosuvastatin alkyl ester;
d) collecting the resulting pure Rosuvastatin alkyl ester.

In the slurry method, the temperature in step (c) is maintained at 0-50° C. preferably between 20-30° C.

This present process provides a method for preparing alkyl esters of Rosuvastatin with low levels of impurities.

The present invention provides a process for preparing Rosuvastatin having low levels of diastereomeric impurity and other contaminants like Rosuvastatin keto ester of Formula III.

The preparation of Rosuvastatin keto ester of Formula III, is elaborated in our PCT application number WO 2008/096257 A1.

Rosuvastatin ethyl ester is prepared as per the procedure given in example 11 of our PCT application No. WO 2008/096257 A1 results in a liquid. It is very difficult to maintain liquid form of intermediate, which may degrade. So, we have developed a process, which yields a crystalline Rosuvastatin ethyl ester.

Powder X-Ray Diffraction (PXRD)

The X-ray powder diffractogram is obtained using a Seifert, XRD 3003 TT system. The X-ray generator was operated at 40 kv and 30 mA, using the Kα line of copper at 1.540598 A° as the radiation source. It is scanned in the diffraction range of 3° to 40° 2θ at a scan rate of 0.03° 2θ per second.

Differential Scanning Calorimetry (DSC)

The thermal behavior of Rosuvastatin ethyl ester is examined by DSC, using Mettler Toledo—instrument Model DSC821$^e$ Differencial Scanning calorimeter caliberated with Indium and Zinc. The sample is heated in a pierced aluminium pan under nitrogen atmosphere at a rate of 10° C./min over a temperature range of 30° C. to 200° C.

The invention is illustrated with the following examples, which are provided by way of illustration only and should not be construed to limit the scope of the invention.

EXAMPLE-1

Preparation of (+) Ethyl 7-[4-(4-Fluorophenyl)-6-Isopropyl-2-(N-Methyl-N-Methylsulfonylamino) Pyrimidin-5-yl]-(3R,5S)-3,5-Dihydroxy-6(E)-Heptenoate (Rosuvastatin Ethyl Ester)

A solution of diethylmethoxyborane in tetrahydrofuran was added (5.24 ml, 4.062 M solution in tetrahydrofuran) to a cold mixture of tetrahydrofuran (60 ml), methanol (13 ml) and ethyl acetate (5 ml) at −75° C. to −80° C. After stirring this mass for 5 min, a solution of ethyl 7-[4-(4-fluorophenyl)-6-isopropyl-2-(N-methyl-N-methylsulfonylamino)pyrimidin-5-yl]-3-oxo-5(S)-hydroxy-6(E)-heptenoate (2 g) prepared in a mixture of tetrahydrofuran (5 ml), methanol (2 ml) and ethyl acetate (3 ml) was added to the above borane solution, while maintaining the temperature at −75° C. to −80° C.

Solid sodium borohydride (0.48 g) was added to the above mixture and the resulting mass was stirred at −75° C. to −80° C. for 5-6 h to ensure completion of reduction. The reaction mass was worked-up and purified from ethyl acetate and heptane.

Yield: 0.8 g
Purity: 99.04%

EXAMPLE-2

Preparation of (+) Ethyl 7-[4-(4-Fluorophenyl)-6-Isopropyl-2-(N-Methyl-N-Methylsulfonylamino) Pyrimidin-5-yl]-3R,5S)-3,5-Dihydroxy-6(E)-Heptenoate (Rosuvastatin Ethyl Ester)

A solution of ethyl 7-[4-(4-fluorophenyl)-6-isopropyl-2-(N-methyl-N-methylsulfonylamino)pyrimidin-5-yl]-3-oxo-5(S)-hydroxy-6(E)-heptenoate (30 g) in a mixture of tetrahydrofuran (75 ml), methanol (30 ml) and ethyl acetate (45 ml) was added to a cold solution of diethylmethoxyborane (17.5 ml of 4.06 M solution in tetrahydrofuran) prepared in a mixture of tetrahydrofuran (900 ml), methanol (195 ml) and ethyl acetate (75 ml) at −75° C. to −80° C. under stirring. Solid sodium borohydride (3.378 g) was added to the above mixture and stirred for 5-6 h for complete reduction. To the reaction mass sequentially added acetone (10 ml) followed by acetic acid (43 ml), water (500 ml), ethyl acetate (300 ml) and allowed to warm to room temperature. The layers were separated and the aqueous layer was extracted second time with ethyl acetate (300 ml). The combined organic layer was washed with brine solution followed by water. The crude product obtained after evaporation of ethyl acetate was co-distilled twice with methanol and crystallized from a mixture of ethyl acetate, ethanol and heptane.

Yield: 24.8 g
Purity: 99.28

EXAMPLE-3

Preparation of (+) Ethyl 7-[4-(4-Fluorophenyl)-6-Isopropyl-2-(N-Methyl-N-Methylsulfonylamino) Pyrimidin-5-yl]-(3R,5S)-3,5-Dihydroxy-6(E)-Heptenoate (Rosuvastatin Ethyl Ester)

A mixture of tetrahydrofuran (60 ml), methanol (13 ml) and toluene (5 ml) was cooled to −78° C. under nitrogen. Diethylmethoxyborane (1.2 ml, 48% w/w in tetrahydrofuran) was added dropwise to the above reaction mixture at −75° C. to −78° C. over a period of 5 min. The mixture was stirred for 5 min at −75° C. to −78° C. and a solution of ethyl 7-[4-(4-fluorophenyl)-6-isopropyl-2-(N-methyl-N-methylsulfonylamino)pyrimidin-5-yl]-3-oxo-5(S)-hydroxy-6(E)-heptenoate (Rosuvastatin keto-ester) (2 g, 0.0039 mol) dissolved in a mixture of tetrahydrofuran (5 ml), methanol (2 ml) and toluene (3 ml) was added at −75° C. to −78° C. over a period of 5 min followed by sodium borohydride (0.225 g, 0.59 mol) in one lot at −78° C. The reaction mixture was stirred at the above temperature and monitored the progress of the reaction by HPLC till disappearance of the Rosuvastatin keto-ester. The mass was quenched with acetone (3 ml) and acetic acid (3 ml) at −78° C. to −75° C. Subsequently, the temperature of the reaction mass was raised to −55° C. and diluted with ethyl acetate (40 ml) and water (40 ml). The temperature was further raised to 25-30° C. and organic layer was separated. The aqueous layer was reextracted with ethyl acetate (25 ml) and the combined organic layer was washed with aqueous sodium bicarbonate solution (8% w/w, 2×40 ml) followed by 25% aqueous sodium chloride (40 ml). The solvent was distilled under reduced pressure (50-100 mm Hg) at 40-45° C. to obtain the crude product as an oily mass, which was crystallized from a mixture of ethyl acetate (4 ml), ethanol (2 ml) and n-heptane (16 ml) at 25-30° C. The product obtained was filtered and dried at 35-40° C. under vacuum.

Yield: 1.7 g
Purity: 99.05%

EXAMPLE-4

Preparation of (+) Ethyl 7-[4-(4-Fluorophenyl)-6-Isopropyl-2-(N-Methyl-N-Methylsulfonylamino) Pyrimidin-5-yl]-(3R,5S)-3,5-Dihydroxy-6(E)-Heptenoate (Rosuvastatin Ethyl Ester)

A mixture of tetrahydrofuran (60 ml), methanol (13 ml) and ethyl acetate (10 ml) was cooled to −78° C. under nitrogen atmosphere and diethylmethoxyborane (1.17 ml, 48% w/w in tetrahydrofuran) was added to it dropwise over a period of 10 min at that temperature. Ethyl 7-[4-(4-fluorophenyl)-6-isopropyl-2-(N-methyl-N-methylsulfonylamino)pyrimidin-5-yl]-3-oxo-5(S)-hydroxy-6(E)-heptenoate (3-Keto-5-hydroxy Rosuvastatin ethyl ester) (2 g, 0.0039 mol) was dissolved in a mixture of tetrahydrofuran (5 ml), methanol (2 ml) and ethyl acetate (6 ml) and added dropwise to the above reaction mass over a period of 15 min at −75° C. to −78° C. Sodium borohydride (0.225 g, 0.0059 mol) was added in one lot at the above temperature. The reaction mass was stirred at −75° C. to −78° C. till the starting material disappeared as monitored by HPLC in the reaction mass. After completion of the reaction, the product was isolated as per the work-up procedure described in the example (3).

Yield: 1.7 g
Purity: 99.17%

EXAMPLE-5

Preparation of (+)-Ethyl 7-[4-(4-Fluorophenyl)-6-Isopropyl-2-(N-Methyl-N-Methylsulfonylamino) Pyrimidin-5-yl]-(3R,5S)-3,5-dihydroxy-6(E)-heptenoate [Rosuvastatin Ethyl Ester]

Diethylmethoxyborane (5 ml, 4 molar solution in tetrahydrofuran) was added to a cooled mixture of tetrahydrofuran (50 ml), methanol (15 ml) and ethyl acetate (6 ml) at −78° C. Sodium borohydride (0.8 gm) was added to the above reaction mass in one lot at −78° C. and stirred for 15 minutes at that temperature before addition of ethyl-7-[4-(4-fluorophenyl)-6-isopropyl-2-(N-methyl-N-methyl sulfonylamino)pyrimidin-5-yl]-3-oxo-(5S)-5-hydroxy-(6E)-heptenoate (3-keto-5-hydroxy Rosuvastatin ethyl ester) [2 gm dissolved in a mixture of tetrahydrofuran (5 ml), ethyl acetate (2 ml) and methanol (2 ml)] over a period of 30 min at −75° C. to −78° C. The above reaction mass was stirred for 2 hours for complete disappearance of the starting material (3-keto-5-hydroxy ethyl Rosuvastatin) by HPLC and quenched by adding to a buffer solution of pH: 3 (100 ml). The organic layer was separated and the aqueous layer was extracted with ethyl acetate (100 ml). The combined organic layer was washed with 2% aqueous sodium bicarbonate (50 ml×2) followed by aqueous sodium chloride (20% w/w, 50 ml). The solvent was distilled out under reduced pressure at 40-45° C. to obtain the product as an oily mass, which was further co-distilled with methanol (50 ml×3) and finally crystallized from isopropyl acetate (7.2 ml) and n-heptane (18 ml).

Yield: 1.53 gm
Purity: 98.84%

EXAMPLE-6

Preparation of Crystalline Form of (+)-Ethyl 7-[4-(4-Fluorophenyl)-6-Isopropyl-2-(N-Methyl-N-Methylsulfonylamino) Pyrimidin-5-yl]-(3R,5S)-3,5-Dihydroxy-6(E)-Heptenoate [Rosuvastatin Ethyl Ester]

Diethylmethoxyborane (134 ml, 4.026 molar solution in tetrahydrofuran) was added to the precooled mixture of tetrahydrofuran (6.9 lt), methanol (1495 ml) and ethyl acetate (575 ml) at −75° to −78° C., over a period of 15 min, followed by addition of sodium borohydride (25.85 gm) in one lot at −75° to −78° C. To the above cooled reaction mass a solution of ethyl-7-[4-(4-fluorophenyl)-6-isopropyl-2-(N-methyl-N-methylsulfonylamino)pyrimidin-5-yl]-3-oxo-(5S)-5-hydroxy-(6E)-heptenoate (3-keto-5-hydroxy Rosuvastatin ethyl ester) [230 gm dissolved in a mixture of tetrahydrofuran (575 ml), ethyl acetate (345 ml) and methanol (230 ml)] was added drop-wise over a period of 30 min at −75° C. to −78° C. The above reaction mass was stirred for 6 h 30 min at −75° to −78° C. After completion of the reaction, the reaction mass was quenched by adding acetone (345 ml) followed by acetic acid (230 ml). Thereafter, DM water (6000 nil), ethyl acetate (3000 ml) and saturated sodium chloride solution (500 ml) was added sequentially to the above reaction mass. The organic layer was separated and the aqueous layer was extracted with ethyl acetate (4000 ml) and the combined organic layer was washed with DM water (6000 ml) followed by aqueous sodium bicarbonate (6000 ml, 7%, w/v) and finally with aqueous sodium chloride (6000 ml, 28% w/v) at 25-30° C. Thus obtained organic layer was concentrated at 40-45° C. under vacuum to yield the crude product of Rosuvastatin ethyl ester.

The crude product of Rosuvastatin ethyl ester was crystallized in a mixture of ethanol, ethyl acetate and n-heptane (1:2:8 v/v) to give crystalline form of Rosuvastatin ethyl ester.
Yield: 184 gm
Purity: 99.36%

EXAMPLE-7

Preparation of Crystalline Form of (+)-Ethyl 7-[4-(4-Fluorophenyl)-6-Isopropyl-2-(N-Methyl-N-Methyl-sulfonylamino) Pyrimidin-5-yl]-(3R,5S)-3,5-Dihydroxy-6(E)-Heptenoate [Rosuvastatin Ethyl Ester]

Diethylmethoxyborane (23.3 ml, 4.026 molar solution in tetrahydrofuran) was added to the precooled mixture of tetrahydrofuran (1.2 lt), methanol (260 ml) and ethyl acetate (100 ml) at −75° to −78° C., over a period of 15 min, followed by addition of sodium borohydride (4.49 gm) in one lot at −75° to −78° C. To the above cooled reaction mass a solution of ethyl-7-[4-(4-fluorophenyl)-6-isopropyl-2-(N-methyl-N-methylsulfonylamino)pyrimidin-5-yl]-3-oxo-(5S)-5-hydroxy-(6E)-heptenoate (3-keto-5-hydroxy Rosuvastatin ethyl ester) [40 gm dissolved in a mixture of tetrahydrofuran (100 ml), ethyl acetate (60 ml) and methanol (40 ml)] was added drop-wise over a period of 25 min at −75° C. to −78° C. The above reaction mass was stirred for 6 h at −75° to −78° C. After completion of the reaction, the reaction mass was quenched by adding acetone (40 ml) followed by acetic acid (40 ml). Thereafter, DM water (400 ml), ethyl acetate (400 ml) and saturated sodium chloride solution (200 ml) was added sequentially to the above reaction mass. The organic layer was separated and the aqueous layer. The aqueous layer was extracted with ethyl acetate (200 ml) and the combined organic layer was washed with aqueous sodium bicarbonate solution (2×800 ml, 7%, w/v), followed by washing with aqueous sodium chloride solution (800 ml) at 25-30° C. Thus obtained organic layer was concentrated at 40-45° C. under vacuum to yield the crude product of the Rosuvastatin ethyl ester.

The crude product of Rosuvastatin ethyl ester was crystallized in a mixture of ethanol, ethyl acetate and n-heptane (1:2:8 v/v) to give crystalline form of Rosuvastatin ethyl ester.
Yield: 35 gm
Purity: 98.99%

EXAMPLE-8

Preparation of (+)-(3R,5S)-7-[4-(4-Fluorophenyl)-6-Isopropyl-2-(N-Methyl-N-Methyl Sulfonylamino) Pyrimidin-5-yl]-3-5-dihydroxy-6(E)-heptenoic acid Calcium Salt (3R,5S)-7-[4-(4-Fluorophenyl)-6-isopropyl-2-(N-methyl-N-methylsulfonylamino)-pyrimidin-5-yl]-3,5-dihydroxy-6 (E)-heptenoic acid ethyl ester (5 g, 0.0098 ml) was dissolved in a mixture of ethanol and tetrahydrofuran (27.5 ml, ethanol:tetrahydrofuran 5:0.5 v/v) at 20° C. and cooled to 10° C. Thereafter, 1N aqueous sodium hydroxide (9.8 ml) was added drop wise to the above reaction mass and stirred at 25-30° C. for 4 h. After completion of the reaction, the solvent was distilled under reduced pressure at 35-40° C. and the residue obtained was dissolved in a mixture of water (48 ml), ethanol (1.5 ml) and tetrahydrofuran (1 ml) at 25° C. It was further extracted using a mixture of toluene:ethyl acetate (6:4 v/v) (12.5 ml×4) at 25° C. The aqueous layer obtained after extraction was filtered through hyflo and concentrated under reduced pressure (20-40 mm Hg) to a volume of ~35 ml at 35-40° C. Aqueous calcium chloride (25 ml) (prepared by dissolving 1.44 g calcium chloride dihydrate in 10 ml of water and making up the volume to 25 ml) was added to the above layer at 25° C. over a period of 1 h during which the product precipitated out. The above suspension was stirred for 3 h at 25-30° C., filtered and washed with water (5×2 ml). Finally, it was dried under reduced pressure (10-20 mm Hg) at 35-40° C. till the moisture content was ~1.8-2%.

Yield: 3.5 g.

We claim:

1. Crystalline polymorphic form of Rosuvastatin ethyl ester of Formula II,

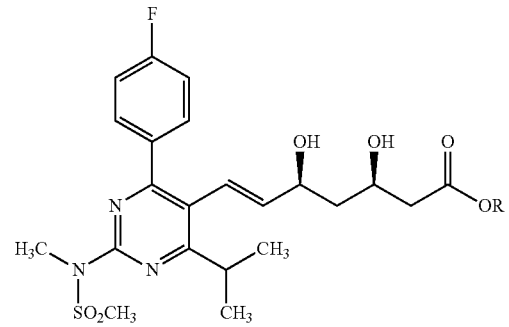

Formula II wherein R represents ethyl, having a X-ray Powder Diffraction having peak reflections at about 9.2, 9.6, 17.3, 18.0, 18.6, 19.4, 21.5, 22.3, 24.2, 24.4, 26.0±0.2 degrees two-theta.

2. Crystalline polymorphic form of Rosuvastatin ethyl ester of Formula II, according to claim 1, is further characterized by having X-ray Powder Diffraction peak reflections at about 8.7, 12.0, 13.7, 15.1, 15.5, 15.8, 16.4, 20.2, 20.6, 21.0, 22.9, 23.5, 24.7, 27.1, 29.2, 30.5, 32.0, 33.1 ±0.2 degrees two-theta.

3. Crystalline polymorphic form of Rosuvastatin ethyl ester of Formula II, according to claim 1, is further characterized by having a Differential Scanning calorimetry (DSC) endothermic peak at about 95.5° C.±1° C.

4. A process for preparing the crystalline polymorphic form of Rosuvastatin ethyl ester of Formula II claimed in claim 1, which comprises:

a) reducing Rosuvastatin keto ester of Formula III,

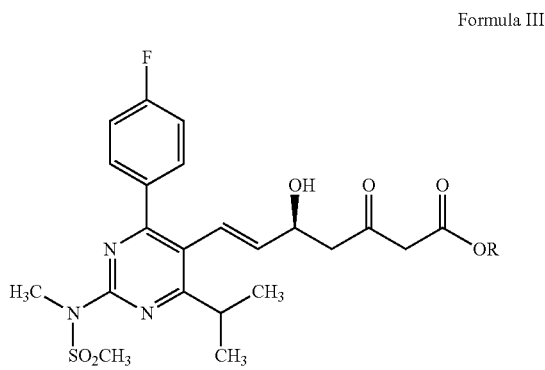

Formula III wherein R represents ethyl
with a hydride ion source and dialkylalkoxyborane at low temperature in a mixture of three or more organic solvents each selected from an ethereal solvent, alcoholic solvent and an aprotic solvent;
b) maintaining the reaction mass at the same temperature under stirring for completion of reaction; and
c) isolating the compound of Formula II.

5. The process according to claim 4, wherein in step (a), the organic solvent is selected from the group consisting of an ethereal solvent selected from $C_2$-$C_8$ ethers or cyclic ethers selected from diethyl ether, dimethyl ether, tetrahydrofuran; alcoholic solvent selected from $C_1$-$C_4$ alcohol and aprotic solvents selected from toluene, alkyl esters selected from ethyl acetate, methyl acetate, chlorinated solvents selected from methylene chloride, chloroform.

6. The process according to claim 4, wherein in step (a) the source of hydride ion is selected from the group consisting of sodium borohydride, potassium borohydride, lithium borohydride and sodium triacetoxy borohydride, which is present in an amount of 1 to about 4 equivalent (based on per gram of Rosuvastatin keto ester of Formula III) and is added at temperature in the range of −50° C. to −95° C.

7. The process according to claim 4, wherein the dialkylalkoxyborane is selected from diethylmethoxyborane, dimethylmethoxyborane, diethylethoxyborane, dimethylethoxyborane, which is in the range of 1-10 m. eq. based on Rosuvastatin keto ester of Formula III.

8. The process according to claim 4, wherein the total volume of solvent mixture used during the reduction step is about 10 volumes to 80 volumes (ml per gram of Rosuvastatin keto ester of Formula III).

9. The process according to claim 4, wherein the Rosuvastatin ethyl ester of Formula II is further recrystallized to obtain pure Rosuvastatin ethyl of Formula II.

10. The process according to claim 4, wherein the Rosuvastatin ethyl ester of Formula II is further converted to Rosuvastatin calcium.

11. The process according to claim 9, which comprises preparing a solution of Rosuvastatin ethyl ester of Formula II, in an organic solvent selected from $C_1$-$C_5$ alcohol selected from methanol, ethanol, butanol; $C_3$-$C_8$ esters selected from ethyl acetate, methyl acetate; $C_3$-$C_8$ ketones selected from methylethyl ketone, methylisobutyl ketone, acetone; $C_6$-$C_{10}$ aromatic hydrocarbons selected from toluene; ethers selected from tetrahydrofuran, methylethyl ether; acetonitrile and mixture thereof and cooling the mass to give Rosuvastatin ethyl ester of Formula II.

12. The process according to claim 11, the Rosuvastatin ethyl ester of Formula II is further converted to Rosuvastatin calcium.

13. The process according to claim 9, which comprises:
a) preparing a solution of Rosuvastatin ethyl ester of Formula II, in an organic solvent selected from $C_1$-$C_5$ alcohol selected from methanol, ethanol, butanol; $C_3$-$C_8$ esters selected from ethyl acetate, methyl acetate; $C_3$-$C_8$ ketones selected from methylethyl ketone, methylisobutyl ketone, acetone; $C_6$-$C_{10}$ aromatic hydrocarbons selected from toluene; ethers selected from tetrahydrofuran, methylethyl ether; acetonitrile and mixture thereof;
b) treating the above solution from step (a) with an antisolvent aliphatic hydrocarbons selected from pentane, hexane, heptane, cyclohexane;
c) stirring the resulting slurry from step (b) for 1 h to 48 h to give pure Rosuvastatin ethyl ester;
d) collecting the resulting pure Rosuvastatin ethyl ester.

14. The process according to claim 13, wherein the Rosuvastatin ethyl ester of Formula II is further converted to Rosuvastatin calcium.

15. A process for preparing Rosuvastatin ethyl ester of Formula II of claim 4,
which comprises:
a) combining Rosuvastatin keto ester of Formula III,

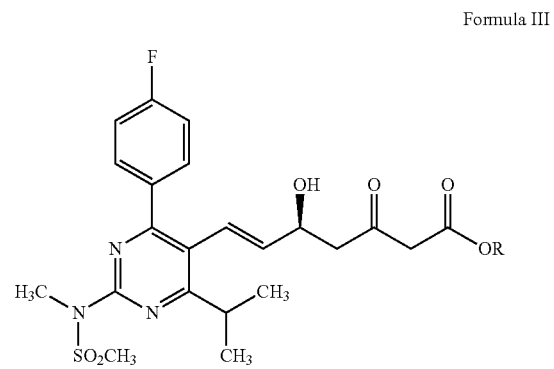

Formula III wherein R is ethyl
with dialkylalkoxyborane at low temperature in a mixture of three or more organic solvents selected each from an ethereal solvent, alcoholic solvent and an aprotic solvent;
b) adding hydride ion source at temperature ranging from −50° C. to −90° C. to the mixture;
c) maintaining the reaction mass at the same temperature under stirring for completion of reaction;
d) isolatinq, the Rosuvastatin ethyl ester of formula II by quenching the reaction mass with water, acid selected from acetic acid, trifluoroacetic acid, base selected from aqueous sodium bicarbonate, aqueous potassium carbonate and peroxide selected from aqueous hydrogen peroxide.

16. The process according to claim 15, wherein the Rosuvastatin ethyl ester of Formula II is further recrystallized to obtain pure Rosuvastatin ethyl ester of Formula II.

17. The process according to claim 15, wherein the Rosuvastatin ethyl ester of Formula II is further converted to Rosuvastatin calcium.

18. A process for preparing Rosuvastatin ethyl ester of Formula II of claim 4, which comprises:
a) combining dialkylalkoxyborane, hydride ion source at low temperature in a mixture of three or more organic solvents selected each from an ethereal solvent, alcoholic solvent and an aprotic solvent;

b) adding a solution of Rosuvastatin keto ester of Formula III to step (a) mixture;

Formula III

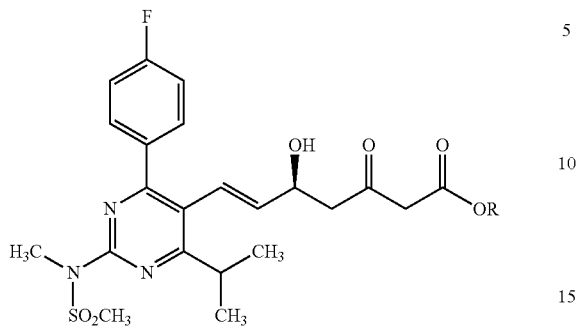

wherein R is ethyl b) maintaining the reaction mass at the same temperature under stirring for completion of reaction;

c) isolating the Rosuvastatin ethyl ester of Formula II by quenching the reaction mass with water, acid selected from acetic acid, trifluoroacetic acid, base selected from aqueous sodium bicarbonate, aqueous potassium carbonate and peroxide selected from aqueous hydrogen peroxide.

19. The process according to claim 18, wherein the Rosuvastatin ethyl ester of Formula II is further recrystallized to obtain pure Rosuvastatin ethyl ester of Formula II.

20. The process according to claim 18, wherein the Rosuvastatin ethyl ester of Formula II is further converted to Rosuvastatin calcium.

* * * * *